United States Patent [19]
Schwartz et al.

[11] Patent Number: 6,121,421
[45] Date of Patent: Sep. 19, 2000

[54] METHODS FOR ISOLATING RECOMBINANT β-CASEIN

[75] Inventors: Ellen M. Schwartz, Waukegan; Harold M. Staack, Highland Park, both of Ill.

[73] Assignee: Abbott Laboratories, Abbott Park, Ill.

[21] Appl. No.: 09/138,474

[22] Filed: Aug. 21, 1998

[51] Int. Cl.$^7$ .............................. C07K 14/52; C12P 21/06
[52] U.S. Cl. ..................... 530/360; 530/361; 530/412; 530/418; 530/427; 435/69.1; 435/71.1; 435/71.2
[58] Field of Search ..................... 530/360, 361, 530/412, 418, 427; 435/69.1, 71.1, 71.2

[56] References Cited

U.S. PATENT DOCUMENTS 5,466,781  11/1995  Dorin et al. ............................ 530/351

FOREIGN PATENT DOCUMENTS

WO 95/16701  6/1995  WIPO .

OTHER PUBLICATIONS

Hansson et al., (*Protein Expression and Purification*, vol. 4, pp. 373–381, 1993.
Simons et al, *Protein Engineering*, vol. 6 No. 7, pp. 763–770, 1993.
Bonnerjea et al, *Bio/Technology*, vol. 4, pp. 954–958, Nov. 1986.
Burgess et al (Acc. Symup. Ser. 578 C Structure and Flow in Surf. Sol.) pp. 380–393, 1994.

*Primary Examiner*—Michael P. Woodward
*Assistant Examiner*—Abdel A. Mohamed
*Attorney, Agent, or Firm*—Cheryl L. Becker

[57] ABSTRACT

The invention provides a method for isolating a protein, specifically β-casein, recombinantly produced in cells that have been genetically engineered to produce the protein. The method involves forming a paste, homogenate or lysate of the cells following fermentation to produce the protein, and performing a two-stage extraction procedure to isolate of the protein. By this method, recombinantly produces β-casein can be isolated with less complexity and greater efficiency than in previously known methods for its isolation.

20 Claims, 1 Drawing Sheet

Fermentation Harvest

↓

Cell Paste/Lysate

↓

↓

↓

Insoluble pellet
containing β-casein
(Discard supernatant)

↓

↓

↓

Supernatant
containing β-casein
(Discard pellet)

Centrifuge/Lyse

1. Suspend in 1st solution

2. Mix/Homogenize

3. Centrifuge

1. Suspend in 2nd solution

2. Mix/Homogenize

3. Centrifuge

Fermentation Harvest

↓            Centrifuge/Lyse

Cell Paste/Lysate

↓            1. Suspend in 1st solution

↓            2. Mix/Homogenize

↓            3. Centrifuge

Insoluble pellet
containing β-casein
(Discard supernatant)

↓            1. Suspend in 2nd solution

↓            2. Mix/Homogenize

↓            3. Centrifuge

Supernatant
containing β-casein
(Discard pellet)

Figure 1

METHODS FOR ISOLATING RECOMBINANT β-CASEIN

FIELD OF THE INVENTION

The invention relates to methods for isolating recombinantly produced proteins from genetically engineered cells. More specifically, the invention relates to methods for isolating β-casein from mixtures of proteins and other cell components and, in particular, from cells genetically engineered to produce β-casein.

BACKGROUND OF THE INVENTION

The proteins in breast milk may provide significant nutritional and other health benefits to infants and adults. Among the proteins that confer such benefits are β-casein, which comprises 80% of the casein in human breast milk. The β-casein in breast milk is believed to serve not only as a source of amino acids required for endogenous protein synthesis, but also as an anti-infective agent and an enhancer of calcium absorption. The addition of β-casein as a supplement to infant formula or other nutritional products may, therefore, provide significant health benefits to infants and adults.

The commercial use of β-casein as a supplement for infant formula or other nutritional products requires the production and isolation of large quantities of the protein at economically reasonable costs. Production of large quantities of β-casein may be accomplished by recombinant production of the protein in bacteria, but such methods require that the protein be efficiently isolated from the complex mixture of other proteins and cell components present in the cell paste, homogenate or lysate obtained after fermentation. Current methods for isolating recombinant proteins often involve precipitating the protein from a suspension. Unless the precipitation is highly specific for the desired protein, however, such methods generally result in high levels of contamination with undesired proteins and other cell components originating from the host cells. In order to remove such contaminants, additional steps of separation and purification may be employed (e.g., HPLC, ion-exchange chromatography), but these are typically costly and time-consuming. In addition, some methods of protein isolation employ denaturing conditions and, therefore, these methods either result in poor yields of functional protein or require additional steps for renaturing the protein. See, e.g., U.S. Pat. No. 5,466,781.

Prior art methods for isolating β-casein from genetically engineered bacterial cells typically involve precipitating the β-casein from a supernatant derived from lysed or fractionated cells. For example, Simons, et al., *Protein Eng.* 6: 763–770 (1993), used genetically engineered *E. coli* to express bovine β-casein. The protein, which accumulated in the periplasmic spaces of the bacteria, was released into a cell suspension by osmotic shock. After centrifugation of the suspension, the β-casein in the pellet was resuspended in a cold water wash and centrifuged again. The β-casein, present in the supernatant, was precipitated by acidification with acetic acid, filtered, and further purified by HPLC. Similarly, Hansson, et al., *Protein Expression and Purif.* 4: 373–381 (1993), used genetically engineered *E. coli* to express β-casein. The β-casein, present in a cell lysate, was precipitated with ammonium sulfate, dissolved in ethanolamine and 6M urea, and further purified by ion-exchange chromatography.

There remains, however, a need in the art for methods for isolating recombinantly produced β-casein that are simpler and more effective than known techniques. The present invention addresses this need by providing methods for isolating large quantities of recombinantly produced β-casein, that are considerably less costly and time-consuming, and result in higher yields with a high degree of purity.

SUMMARY OF THE INVENTION

In general, the present invention relates to methods for isolating a recombinantly produced protein from cells which have been genetically engineered to produce the protein. In particular, the invention provides methods for isolating recombinantly produced β-casein from cells genetically engineered to produce the protein. In preferred embodiments, the β-casein is human β-casein, and the cells are prokaryotic cells such as *E. coli*.

In one embodiment, the present invention provides for methods of isolating recombinant β-casein from prokaryotic cells genetically engineered to produce β-casein, by obtaining a crude preparation of said cells (e.g., a homogenate, lysate, or cell paste), mixing the crude preparation with a first solution comprising a buffer system in which the β-casein is substantially insoluble, centrifuging the first suspension to obtain a first pellet and a first supernatant, wherein the first pellet includes substantially all of the β-casein, suspending the first pellet in a second solution comprising a buffer system and a protein solubilizing agent in which the β-casein is substantially soluble, and centrifuging the second suspension to obtain a second pellet and a second supernatant, in which the second supernatant includes substantially all of said β-casein.

In preferred embodiments, the first solution comprises a buffer system at a pH of between about 7.0 and about 8.5, and the second solution comprising a buffer system at a pH of between about 7.5 and about 9.8. In addition, the second solution preferably includes a protein solubilizing agent, such as urea or guanidine-HCl. In most preferred embodiments, the protein solubilizing agent is urea at a concentration between about 2.5 M and 8.0 M.

In some preferred embodiments, the first solution and/or second solution further includes a protease inhibitor, such as PMSF, aprotinin, leupeptins, pepstatin A, antipain, TLCK, and TPCK. In most preferred embodiments, the protease inhibitor is PMSF at a concentration between about 0.1 mM and 10 mM.

In some preferred embodiments, the first solution and/or second solution further includes a chelating agent, such as EDTA or other chelating agents capable of binding calcium ions. In most preferred embodiments, the chelating agent is EDTA at a concentration between about 0.1 mM and 5.0 mM.

The methods of the present invention may be practiced with any of a number of standard buffer systems, with the pH preferably adjusted as described above. Thus, for example, preferred buffer systems include Tris, Tris/Tween, Tris/Triton, Tris/urea, Tris-buffered saline, Tris-buffered phosphate, MOPS, guanidine, ethanolamine, sodium borate, phosphate, and urea buffers.

In all embodiments, the preferred β-casein is a recombinant, non-phosphorylated β-casein produced by recombinantly engineered bacteria, preferably *E. coli*. In addition, in all preferred embodiments, the preferred β-casein is human β-casein. In accordance with the present invention, the β-casein may be isolating in the second supernatant, or may be further concentrated or purified by standard methods known in the art.

BRIEF DESCRIPTION OF THE DRAWINGS

FIG. 1 is a flowchart describing a preferred embodiment of the methods of the invention.

DETAILED DESCRIPTION OF THE INVENTION

The present invention provides methods for isolating β-casein, particularly β-casein, from mixtures of proteins and other cell components and, in particular, from cell pastes, homogenates or lysates produced from cells that have been genetically engineered to express β-casein. Unlike prior art methods, which require costly and time-consuming isolation and purification steps such as HPLC or ion-exchange chromatography, the current methods result in a high yield and high degree of purity using a simple series of suspensions and precipitations. In brief, the present methods exploit the solubility characteristics of β-casein to substantially isolate and purify the protein in two stages. The methods of the present invention will, therefore, also be useful in the isolation of proteins with solubility characteristics similar to those of β-casein.

Thus, the present invention provides for methods of isolating recombinant β-casein from prokaryotic cells genetically engineered to produce β-casein, by obtaining a crude preparation of said cells (e.g., a homogenate, lysate, or cell paste) and (1) mixing the crude preparation with a first solution comprising a buffer system in which the β-casein is substantially insoluble, centrifuging the first suspension to obtain a first pellet and a first supernatant, wherein the first pellet includes substantially all of the β-casein, and (2) suspending the first pellet in a second solution comprising a buffer system and a protein solubilizing agent in which the β-casein is substantially soluble, and centrifuging the second suspension to obtain a second pellet and a second supernatant, in which the second supernatant includes substantially all of said β-casein. As used herein, a protein is said to be "substantially soluble" in a solution if, after thorough mixing (e.g., by tissumizer, homogenizer, stir bar, agitator), the percentage of the protein which remains in solution is at least about 75%, preferably 80%, and most preferably 85%. Conversely, as used herein, a protein is said to be "substantially insoluble" in a solution if, after thorough mixing, the percentage of the protein which precipitates out of the solution is at least about 75%, preferably 80%, and most preferably 85%. After centrifugation of a suspension of a protein and a solution, the resulting pellet or supernatant is said to include "substantially all" of the protein if the pellet or supernatant includes at least about 75%, preferably 80%, and most preferably 85%.

The methods of the present invention may be practiced on any standard, crude preparation of β-casein, such as a cell paste, homogenate or lysate obtained from a fermentation of cells genetically engineered to express β-casein. Thus, for example, prokaryotic cells, such as Escherichia (e.g., E. coli-β, BL21(DE3) or K-12), Bacillus, Lactobacillus, and Streptococcus species may be genetically engineered to produce β-casein by inserting DNA sequences encoding the protein into an appropriate expression vector and transfecting the cells. See, e.g., Hansson et al., (1993); Simons et al. (1993). As described below, E. coli-β cells have been used to express a non-phosphorylated form of β-casein which forms inclusion bodies in the cells, and which may be isolated according to the methods described herein. Whichever bacterial host is employed, it is preferred that the β-casein sequences are operably joined to a strong promoter that is either constitutive or inducible. The cells are grown in a fermentation vessel and, if necessary, induced to express the β-casein protein. After allowing a period for the cells to express the β-casein, the cells are harvested. At this point, the cells may simply be centrifuged to form a cell paste or pellet, or they may be homogenized or lysed by standard chemical or mechanical means (e.g., homogenization, sonication).

In the first stage of the methods of the present invention, a cell paste, homogenate or lysate containing β-casein is suspended in a first solution which solubilizes at least some contaminants but which does not substantially solubilize β-casein. If the starting material contains intact cells, as when a cell paste is the starting material, the cells may be mixed with the first solution and subjected to standard mechanical means for disrupting the cells (e.g., homogenization, sonication), or chemical lytic agents may be included in the first solution (e.g., lysozyme) to cause cell lysis. Alternatively, the cells may be disrupted or lysed by standard means to form a cell homogenate or lysate prior to mixing with the first solution. In either case, the resulting first suspension is then thoroughly mixed or homogenized (e.g., using a tissumizer, or a homogenizer at 700 bar for 1 hr) and then centrifuged (e.g., using a continuous flow centrifuge at 500 ml/min) to form a first pellet and a first supernatant. The β-casein is largely contained in the first pellet and the first supernatant is, therefore, discarded. Optionally, the pellet may be resuspended in a fresh volume of the first solution, mixed and centrifuged again, discarding the supernatant as before. This is not recommended, however, as it may result in a lower final yield of β-casein.

The first solution comprises a standard buffer system in which β-casein is largely insoluble whereas at least some contaminants remain in solution. In accordance with the present invention, it has been found that a large variety of standard buffer systems may be employed in which the pH is maintained between about 7.0 and 8.5, preferably between 7.2 and 8.0, most preferably about 7.5, with the initial pH adjusted as needed by the addition of acid (e.g., HCl) or base (e.g., NaOH). For example, the buffer system may comprise Tris in an aqueous solution at a concentration of between about 20 mM and 60 mM, preferably about 50 mM. Alternative buffer systems useful in the invention include Tris/Tween (e.g., 50 mM Tris; 0.5–2% Tween, preferably 1% Tween), Tris/Triton (e.g., 50 mM Tris; 0.5–2% Triton, preferably 1% Triton), MOPS buffers (e.g., 20–60 mM), sodium borate buffers (e.g., 30–60 mM), and phosphate buffers (e.g., 20–60 mM), all of which are well known in the art. In addition, the first solution optionally may comprise a chelating agent, preferably EDTA at a concentration of between about 0.1 mM and 5 mM, preferably about 1–2 mM. In addition, a protease inhibitor optionally may be added, such as PMSF at a concentration of between about 0.1 mM and 10 mM, preferably about 1 mM; aprotinin at a concentration of between about 0.1 and 20 μg/ml, preferably about 1–2 μg/ml; leupeptins at a concentration of between about 0.1 and 20 μg/ml, preferably about 1–2 μg/ml; pepstatin A at a concentration of between about 0.1 and 10 μg/ml, preferably about 1 μg/ml; antipain at a concentration of between about 0.1 and 20 μg/ml, preferably about 1–2 μg/ml; TLCK (tosyllysine chloromethyl ketone) at a concentration of between about 5 and 500 μg/ml, preferably about 50 μg/ml; TPCK (tosylphenylalanine chloromethyl ketone) at a concentration of between about 10 and 1000 μg/ml, preferably about 100 μg/ml; or any other protease inhibitor known in the art. As noted above, the first solution optionally may also contain chemical lytic agents if unlysed cells are present.

In the second stage of the methods of the present invention, the pellet from the first stage is suspended in a second solution that solubilizes β-casein but which does not solubilize some of the remaining contaminants. The resulting second suspension is then thoroughly mixed or homogenized (e.g., using a tissumizer, or a homogenizer at 750 bar for 20 min), and centrifuged (e.g., using a continuous flow centrifuge at 500 ml/min) to form a second pellet and a second supernatant. The β-casein is largely contained in the second supernatant and the second pellet is, therefore, discarded. Optionally, the second supernatant may be mixed with a fresh volume of the second solution, and centrifuged again, discarding the pellet as before. As described below, it is currently preferred that this step be repeated at least once, as it does not appear to significantly decrease yield, while resulting in an improved degree of purification.

The second solution comprises a standard buffer system in which β-casein is largely soluble whereas at least some contaminants remain insoluble. In accordance with the present invention, it has been found that a large variety of standard buffer systems may be employed in which the pH is maintained between about 7.5 and 9.8, preferably between 8.2 and 9.0, most preferably about 8.5, with the initial pH adjusted as needed by the addition of acid (e.g., HCl) or base (e.g., NaOH). In addition, it has been found that the inclusion of a protein solubilizing agent such as urea or guanidine-HCl significantly enhances the solubility of β-casein in buffers at higher pH and, therefore, such an agent is included in the second solutions of the invention. Thus, for example, the buffer system may comprise Tris in an aqueous solution at a concentration of between about 20 mM and 60 mM, preferably about 50 mM, and urea at a concentration of between about 2.5 M and 8.0 M, preferably between 3.0 M and 7.0 M, most preferably about 6 M, with the initial pH adjusted as needed by the addition of acid (e.g., HCl) or base (e.g., NaOH). Alternative buffer system include guanidine buffers (e.g., 4–6 M) and ethanolamine buffers (e.g., 30–60 mM), all of which are well known in the art. The ethanolamine buffer system would require the use of a protein solubilizing agent, preferably urea. In addition, the second solution optionally may comprise a chelating agent, preferably EDTA at a concentration of between about 0.1 mM and 5.0 mM, preferably about 1–2 mM. Alternatively, another calcium-binding chelating agent may be employed. In addition, a protease inhibitor optionally may be added, such as PMSF at a concentration of between about 0.1 mM and 10 mM, preferably about 1 mM; aprotinin at a concentration of between about 0.1 and 20 μg/ml, preferably about 1–2 μg/ml; leupeptins at a concentration of between about 0.1 and 20 μg/ml, preferably about 1–2 μg/ml; pepstatin A at a concentration of between about 0.1 and 10 μg/ml, preferably about 1 μg/ml; antipain at a concentration of between about 0.1 and 20 μg/ml, preferably about 1–2 μg/ml; TLCK (tosyllysine chloromethyl ketone) at a concentration of between about 5 and 500 μg/ml, preferably about 50 μg/ml; TPCK (tosylphenylalanine chloromethyl ketone) at a concentration of between about 10 and 1000 μg/ml, preferably about 100 μg/ml; or any other protease inhibitor known in the art.

Depending on the ultimate application, the β-casein in second supernatant may be stored and/or utilized in this form, or may be concentrated from the supernatant by, for example, dialysis, column chromatography, or other standard methods.

The present invention may be better understood upon consideration of the following non-limiting examples. The following examples illustrate methods for engineering bacteria that will produce β-casein, methods for fermenting such cells to produce β-casein, and methods according to the present invention for the isolation of β-casein from cells obtained from the fermentation. The following examples are provided only for the purposes of illustrating certain preferred embodiments of the invention.

As will be clear to the skilled artisan, other genetically engineered prokaryotic cells, as well as other methods of fermentation suitable to those cells, may be used to recombinantly produce the β-casein. Thus, the following examples are provided merely for purposes of illustrating preferred embodiments of the invention. Accordingly, the scope of the invention is limited only by the scope of the appended claims.

EXAMPLES

Example 1

Production of Genetically Engineered Bacteria $E.$ $coli$-β were genetically engineered to produce human β-casein by introduction of a plasmid bearing the DNA sequence encoding human β-casein. The general method, including the plasmid construct BL21(DE3)(pS26), are described in Hansson et al. (1993), supra.

Example 2

Fermentations

Using the above-described $E.$ $coli$-β, human β-casein was produced recombinantly in a series of fermentations. First, three 10 L fermentations were conducted to test the performance of the $E.$ $coli$-β in producing human β-casein under differing conditions. Following these three fermentations, a fourth, large-scale fermentation was conducted.

A. Fermentation 1

Fermentation 1 was conducted in 10 L of medium containing 2.4% yeast extract, 1.2% tryptone, 0.5% glycerin, 1.14% $K_2HPO_4$, and 0.17% $KH_2PO_4$ ("standard medium"). Fermentation 1 was grown at 37° C., 500 rpm, 1.5 VVM, 1.0% inoculum, induced in mid-log phase (OD of about 10.8) at 7 hr elapsed fermentation time (EFT), and harvested at four hours post-induction (HPI).

The growth characteristics (pH, OD, etc.) were typical for $E.$ $coli$ in this medium. The final OD was 15.2 and a direct microscopic examination (DME) did not show significant inclusion bodies. The final biomass yield was about 185 g wet weight.

B. Fermentation 2

Fermentation 2 was conducted similarly to Fermentation 1, except that it was induced at the beginning of the fermentation to simulate a constitutive expression system. It was sampled at the same time points as Fermentation 1 and harvested at the same time as Fermentation 1.

This fermentation grew much more slowly than Fermentation 1, possibly due to the added stress of the expression of the β-casein. Whereas Fermentation 1 had an OD of almost 11 at 7 hr EFT and ended at an OD of 15, Fermentation 2 had a OD of 0.5 at 7 hr EFT and ended at about 10. Again a DME showed no inclusion bodies. The final biomass yield was about 185 g wet weight.

C. Fermentation 3

Fermentation 3 was also conducted similarly to Fermentation 1, except that it was necessary to add NaOH to control the pH to between about 7.0 and 7.5. Cells were harvested at 6 HPI.

Fermentation 3 ran similarly to Fermentation 2, but was slightly slower. The OD at the point of induction was about 9 at 7 hr EFT. The final OD was 19 at 6 HPI. The final biomass yield was 220 g wet weight.

SDS-PAGE of proteins from the three fermentations indicated that the expression of protein in Fermentation 1 and in Fermentation 3 was comparable. The expression in Fermentation 2 was very low. In general, it was found that the β-casein was ⅓ soluble and ⅔ insoluble in these fermentations.

D. Large-scale Fermentation

A 750 L fermentation was run in the standard medium and was grown at 37° C., 100 rpm, 0.75 VVM, 0.1% inoculum, induced at an OD of 3.9 at about 6 hr EFT, and harvested at 5 HPI.

A one hour sample DME revealed the presence of inclusion bodies in the cells. This was not unexpected because the β-casein was fairly insoluble in Fermentation 2. In addition, this fermentation was induced earlier than Fermentations 1 and 2 and, therefore, higher expression of β-casein was not unexpected. By the end of the fermentation the inclusion bodies had grown fairly large and much of the culture had several inclusion bodies per cell. The fermentation seemed complete at 4 HPI with the OD only increasing from 20.2 to 20.7 from 4 to 5 HPI. Again the growth characteristics (pH, OD, etc.) were typical for E. coli in this medium. The final biomass yield was about 13.8 kg wet weight. SDS-PAGE indicated that the human β-casein was at least 30–40% of total cell protein.

Example 3

Isolation of Human β-casein

After fermentation of the bacteria to produce human β-casein, the protein was isolated from the fermentation broth. An outline of the method is shown in the flowchart at FIG. 1. A cell paste was first formed by centrifuging the product of the fermentation. Approximately 8.7 kg of cell paste was then suspended in 43 L of a solution containing 50 mM Tris, 1 mM EDTA, and 1 mM PMSF, and water at pH 7.5 ("first solution"). The suspension was passed through a homogenizer twice at about 700 Bar to disrupt the cells and separate soluble and insoluble E. coli proteins. The insoluble proteins were pelleted by continuous flow centrifugation to form a "first pellet" and "first supernatant", and the first supernatant was discarded. The first pellet was then washed in another 43 L of the first solution and re-pelleted in the centrifuge before storing at −2 to 8° C. overnight.

After the first centrifugation, the yield was about 1950 g wet weight from the 8.7 kg cell paste. The yield after washing and re-pelleting was about 1100 g wet weight from the 1950 g of starting material. SDS-PAGE analysis of the fractions indicated that the majority of human β-casein remained in the first pellet with little going into the first supernatant following the first centrifugation. After re-suspension, wash, and second centrifugation of the first pellet, however, the supernatant had a significant β-casein band. The protein level in this wash supernatant was only about 2 mg/ml by Bio Rad assay, but there was over 40 L of this discarded, resulting in a loss of about 80 g of protein. Because of this loss, it is currently preferred that a single wash be performed, in approximately 87 L of the first solution. Nonetheless, the purity of the final first pellet was determined by SDS-PAGE to be about 95%.

The 1100 g of the washed first pellet was re-suspended in about 5.5 L (5×) 6 M Urea, 50 mM Tris, 2 mM EDTA, 1 mM PMSF, and water at pH 7.5 ("second solution"). The suspension was passed through a homogenizer once at about 750 Bar. The suspension was clarified by continuous flow centrifugation to form a "second pellet" and "second supernatant," and the second pellet was discarded. The second supernatant was then passed through a filter train consisting of a Pall Profile depth prefilter, a Pall 0.65 μm prefilter and a Pall 0.2 μm absolute final filter. The filtrate was stored at −2 to 8° C.

From the 1100 g of the first pellet, there was only about 20–30 g of insoluble material discarded after the centrifugation. The material filtered well with little pressure buildup on the filters. SDS-PAGE analysis of the fractions indicated that there was little change in the protein levels during the processing and that resuspending the material using only a tissumizer, rather than a homogenizer, may be sufficient before filtration. The final protein concentration was about 25 mg/ml by the Bio Rad assay, with a final yield of about 5 L resulting in a total of 125 g β-casein. The purity of the protein as assessed by HPLC was about 96%.

Example 4

Dialysis of β-casein

Supernatant containing the β-casein at 95% purity (as obtained in Example 3) was dialyzed into dialyzing solutions comprising different buffer systems. Briefly, 10 ml of the supernatant containing the β-casein was dialyzed against 500 ml of the corresponding buffers using 6,000–8,000 MW cut-off dialysis bags at 2–8° C. for 18 hours. The purpose of this step was to prepare the material for lyophilization.

The table below describes the results of dialysis of β-casein into a variety of buffers:

| Dialysis of β-casein (95% Purity) from Second Supernatant | | |
|---|---|---|
| Dialysis into | % Yield | Purity by HPLC |
| TRIS, pH 7.5 | 65% | 93% |
| TRIS, pH 8.5 | 82% | 91% |
| Ethanolamine, pH 9.5 | 82% | 89% |
| Ethanolamine/NaCl, pH 9.0 | 65% | 95% |
| PBS, pH 7.2 | 9.0% | 29% |

As shown in the table, dialysis of β-casein from the supernatant generally does not increase product purity. In addition, dialysis reduced overall yield, particularly dialysis against PBS buffer. Therefore, for some applications, such dialysis may not be desirable.

What is claimed is:

1. A method for isolating recombinant β-casein from prokaryotic cells genetically engineered to produce β-casein, consisting of the steps of:

obtaining a crude preparation of said cells;

mixing said preparation with a first solution comprising a buffer system, wherein said β-casein is substantially insoluble in said first solution;

centrifuging said first suspension to obtain a first pellet and a first supernatant, wherein said first pellet includes substantially all of said β-casein;

suspending said first pellet in a second solution comprising a buffer system and a protein solubilizing agent, wherein said β-casein is substantially soluble in said second solution; and centrifuging said second suspension to obtain a second pellet and a second supernatant, wherein said second supernatant includes substantially all of said β-casein.

2. A method for isolating recombinant β-casein from prokaryotic cells genetically engineered to produce β-casein, consisting of the steps of:

obtaining a crude preparation of said cells;

mixing said preparation with a first solution comprising a buffer system at a pH of between about 7.0 and about 8.5 to form a first suspension;

centrifuging said first suspension to obtain a first pellet and a first supernatant, wherein said first pellet includes substantially all of said β-casein;

suspending said first pellet in a second solution comprising a buffer system at a pH of between about 7.5 and about 9.8 to form a second suspension; and centrifuging said second suspension to obtain a second pellet and a second supernatant, wherein said second supernatant includes substantially all of said β-casein.

3. The method of claim 2, wherein said second solution further comprises a protein solubilizing agent.

4. The method of claim 3, wherein said protein solubilizing agent is selected from the group consisting of urea and guanidine-HCl.

5. The method of claim 4, wherein said protein solubilizing agent is urea at a concentration between about 2.5 M and 8 M.

6. The method of claim 2, wherein said first solution further comprises a protease inhibitor.

7. The method of claim 2, wherein said second solution further comprises a protease inhibitor.

8. The method of claims 6 or 7, wherein said protease inhibitor is selected from the group consisting of phenylmethylsulphonylfluoride (PMSF), aprotinin, leupeptins, pepstatin A, antipain, tosyllysine chloromethyl ketone (TLCK), and tosylphenylalanine chloromethyl ketone (TPCK).

9. The method of claim 8, wherein said protease inhibitor is PMSF at a concentration between about 0.1 mM and 10 mM.

10. The method of claim 2, wherein said first solution further comprises a calcium ion chelating agent.

11. The method of claim 2, wherein said second solution further comprises a calcium ion chelating agent.

12. The method of claims 10 or 11, wherein said chelating agent is ethylenediaminetetraacetic acid (EDTA).

13. The method of claim 12, wherein said EDTA is at a concentration between about 0.1 mM and 5 mM.

14. The method of claims 1 or 2, wherein said buffer system comprises Tris at a concentration of between about 20 mM and 60 mM.

15. The method of claims 1 or 2, where said buffer system comprises Tris at a concentration of between about 20 mM and 60 mM and Tween at a concentration of between about 0.5% and 2%.

16. The method of claims 1 or 2, wherein said buffer system comprises Tris at a concentration of between about 20 mM and 60 mM and Triton at a concentration of between about 0.5% and 2%.

17. The method of claims 1 or 2, wherein said buffer system comprises 3-(N-morpholino)propanesulfonic acid (MOPS) at a concentration of between about 20 mM and 60 mM.

18. The method of claims 1 or 2, wherein said buffer system comprises ethanolamine at a concentration of between about 30 mM and 60 mM.

19. The method of claims 1 or 2, wherein said buffer system comprises sodium borate at a concentration of between about 30 mM and 60 mM.

20. The method of claims 1 or 2, wherein said buffer system comprises phosphate at a concentration of between about 20 mM and 60 mM.

* * * * *